United States Patent [19]
Wechter et al.

[11] Patent Number: 5,846,967
[45] Date of Patent: Dec. 8, 1998

[54] NATRIURETIC AND ANTI-HYPERTENSIVE COMPOUNDS

[75] Inventors: William J. Wechter; E. David Murray, Jr.; Darko Kantoci, all of Redlands, Calif.

[73] Assignee: Loma Linda University Medical Center, Loma Linda, Calif.

[21] Appl. No.: 822,046

[22] Filed: Mar. 24, 1997

Related U.S. Application Data

[63] Continuation of Ser. No. 275,553, Jul. 15, 1994, abandoned.
[51] Int. Cl.$^6$ .......................... C07D 281/10; A61K 31/55
[52] U.S. Cl. ............................................ 514/211; 540/491
[58] Field of Search .............................. 540/491; 514/211

[56] References Cited

FOREIGN PATENT DOCUMENTS

A-0 278 449   8/1988   European Pat. Off. .

OTHER PUBLICATIONS

Yeung, P.K.F., et al. "Pharmacokinetics and Metabolism of Diltiazem in Healthy Males and Females Following a Signal Oral Dose" Eur. J. Drug Metab. Pharmacokinet., vol. 18 pp. 119–206 (1993), pp. 200 and 204 only.

Y. Sugawara, et al. "Metabolism of Diltiazem I. Structure of New Acidic and Basic Metabolities in Rat, Dog and Man" J. Pharmacobio–Dyn. 11, 211–223 (1988), p. 221 only.

Murata, K. et al. "Pharmacokinetics of Diltiazem and Its Metabolities in Dogs After Oral Adminstration" Pharmaceatuical Research 10, 1165–8 (1993), p. 1166 only.

Maurer, Arch. Toxicol. 64, 218(1990).

H. Inoue et al., "Synthesis of Halogen–Substituted 1,5–Benzothiazepine Derivaties and Their Vasodilating and Hypotensive Activities," J. Med. Chem., vol. 34, No. 2, pp. 675–687 (1991).

*Primary Examiner*—Mark L. Berch
*Attorney, Agent, or Firm*—Knobbe, Martens, Olson & Bear LLP

[57] ABSTRACT

A compound having the formula I

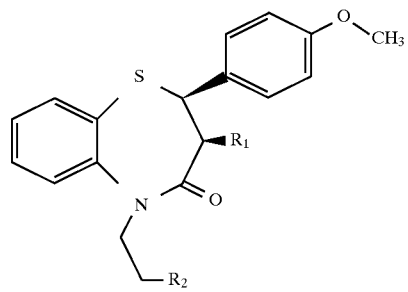

in which $R_1$, $R_2$ independently are OH, OOC—$R_3$ or O—$R_3$, and $R_3$ is an unsubstituted or substituted $C_1$–$C_6$ alkyl, alkenyl, alkynyl or phenyl group.

The compound is useful as a natriuretic and anti-hypertensive agent.

5 Claims, No Drawings

NATRIURETIC AND ANTI-HYPERTENSIVE COMPOUNDS

This application is a continuation of application Ser. No. 08/275,553, filed Jul. 15, 1994 abandoned.

BACKGROUND OF THE INVENTION

1. Field of the Invention

This invention relates to compounds which can be used to increase sodium excretion and reduce blood pressure in man or other mammals. The invention also relates to methods for synthesis of the compounds, and to methods for therapeutic treatment of mammals for increasing sodium excretion and lowering blood pressure.

2. History of Related Art

The adverse effects of high sodium concentration are considered to be partially responsible for a number of diseases, including hypertension, congestive heart failure, ischemia, cirrhosis of the liver and renal disease leading to chronic renal failure. Understanding the nature of the system controlling sodium excretion and blood pressure, therefore, may lead to an effective therapy or cure for these diseases.

Thus, it would be highly desirable to provide compounds having a natriuretic effect or hypotensive effect. It would also be desirable to develop new pharmaceutical compounds or new methods to treat sodium excretion related disease and hypertension.

SUMMARY OF THE INVENTION

One aspect of the present invention provides natriuretic, anti-hypertensive compounds having the formula I

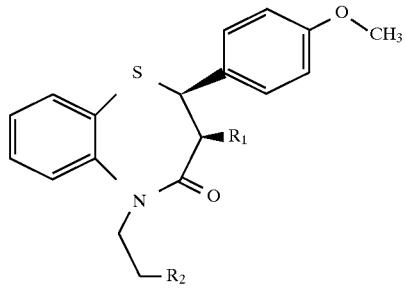

in which
$R_1$, $R_2$ independently are OH, OOC—$R_3$ or O—$R_3$, and $R_3$ is an unsubstituted or substituted $C_1$–$C_6$ alkyl, alkenyl, alkynyl or phenyl group.

In a preferred embodiment, $R_1$ and $R_2$ are OH.

Another aspect of present invention provides a pharmaceutical composition useful for stimulating sodium excretion in the urine of a mammal and for reducing blood pressure. The pharmaceutical composition comprises a pharmaceutically acceptable carrier and a compound as described above in an amount effective to stimulate sodium excretion and anti-hypertensive activity. The compositions can also comprise a mixture of two or more of the compounds of the invention, with the total amount of the compounds being effective for the indicated action.

Still another aspect of the present invention provides a method of treating a mammal suffering from hypertension or an edematous condition. The method comprises the step of orally or parenterally administering a pharmaceutical composition of present invention to the mammal.

The invention is defined in its fullest scope in the appended claims and is described below in its preferred embodiments.

DETAILED DESCRIPTION OF THE PREFERRED EMBODIMENTS

In accordance with the present invention, novel compounds and methods of synthesizing the compounds are provided. The compounds can be used for stimulating sodium excretion and lowering blood pressure in mammals and for treating high sodium concentration related diseases in humans.

A compound of present invention has the formula I

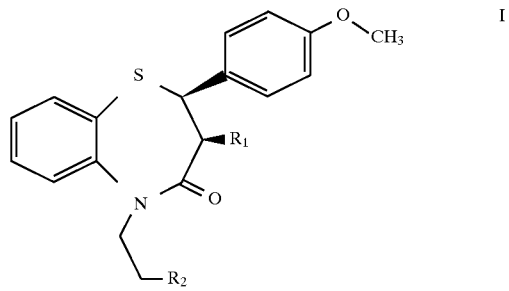

in which
$R_1$, $R_2$ independently are OH, OOC—$R_3$ or O—$R_3$, and $R_3$ is an unsubstituted or substituted $C_1$–$C_6$ alkyl, alkenyl, alkynyl or phenyl group.

In preferred embodiments, $R_1$ and $R_2$ are OH or lower alkanoyl groups. $R_3$ in such groups preferably is a lower aliphatic group such as methyl, ethyl, propyl, butyl, isobutyl, sec-butyl, tert-butyl, pentyl or neo-pentyl, or a phenyl group.

$R_3$ can be unsubstituted or substituted with one or more substituent such as alkyl, aryl, alkaryl, aralkyl, ether or halogen.

In a particularly preferred embodiment, $R_1$ and $R_2$ are OH. The compound having this particular structure is designated LLU-β1.

Compounds of the present invention are shown to have natriuretic, diuretic and anti-hypertensive activity in mammals. A compound has "natriuretic activity" if it increases the rate of sodium excretion in a mammal upon administration to the mammal. Preferably, the compound increases the rate of sodium excretion and tends to produce an equilibrium level of sodium in the extra-cellular fluid without increasing the excretion of potassium.

The term "compound" refers to both the native compound and in vitro or in vivo modifications which retain biologic activity. It is understood that limited modifications, substitutions or deletions of functional groups may be made without destroying the biological activity. Moreover, it will be recognized by those skilled in the arts of chemistry and pharmaceutical preparation that many derivatives can be made which are biologically and chemically equivalent to, or even more active than, the compounds disclosed herein.

Furthermore, compounds of the present invention can be mixed with, bonded to or conjugated with compounds having the same or a complementary range of biological activities to obtain the benefits of the present invention.

The biological activity of compounds of present invention can be determined by a number of assay techniques which include, but are not limited to, the in vivo bioassay to measure the natriuresis and the mean arterial pressure (MAP) in conscious rats after infusion of the compounds of present invention into conscious rats as well as standard natriuretic or anti-hypertensive assays in the rats. The compounds of the present invention are shown to have natriuretic, diuretic and anti-hypertensive activity in the in vivo bioassay. For example, in the in vivo bioassay, natriuresis can be observed when a compound of the present invention is infused to the conscious rat.

Compounds of the present invention can find use in numerous therapeutic applications, such as, e.g., inducing natriuresis and diuresis. Thus, these compounds can find use as therapeutic agents in the treatment of various edematous states such as, for example, congestive heart failure, cirrhosis of the liver accompanied by edema or ascites, in addition to hypertension and renal failure due to ineffective renal perfusion or reduced glomerular filtration rate. The compounds of the present invention may also be used to treat conditions such as ischemia.

A compound according to the invention can be administered to a mammal for veterinary use, such as with domestic animals, and clinical use in humans in a manner similar to other therapeutic agents, that is, as a composition which includes one or more natriuretic and/or anti-hypertensive compounds of the present invention together with a physiologically acceptable carrier.

The amount of the inventive natriuretic and anti-hypertensive compound, or compounds, administered is therapeutically effective if it can increase sodium excretion. A typical initial dose would be from 0.1 mg/kg to 3 mg/kg of host body weight, and one or more times per day. Later doses can be adjusted in accordance with the clinical effects of the initial dose. The total daily dose can consist of a single individual dose or multiple doses given at intervals. Dosages within these ranges can be administered by constant infusion over an extended period of time, usually exceeding 24 hours, until the desired therapeutic benefits have been obtained.

The active compounds can be administered neat, as mixtures with other physiologically acceptable active or inactive materials such as moistening agents, flavoring agents, binding agents, and extenders, as well as other compounds having pharmacological activities, such as other diuretics which increase the distal delivery of sodium or other natriuretic or anti-hypertensive agents. It may also be administered with physiologically suitable carriers such as, for example, water or normal saline. The compounds can be administered orally or parenterally, for example, by injection. Injection can be subcutaneous, intravenous, or by intramuscular injection.

The inventive pharmaceutical compositions can take the form of tablets, capsules, injectable solutions and suspensions, oral solutions, and other formulations intended for pharmaceutical use. For example, a composition intended for use in a tablet could contain a natriuretic and/or anti-hypertensive compound of the invention as the active material, together with calcium stearate, calcium sulfate, microcrystalline cellulose, peppermint oil, polysorbate 80, povidone, and pregelatinized starch.

Compounds of the present invention can be obtained by several methods. For example, they can be obtained by chemical synthetic methods known to those skilled in the art. One such method is the method described by Y. Sugawara et al., Pharmacobio-Dyn. 11, 211–223 (1988). Another such method is the method described by H. Inoue, *J. Med. Chem.*, 34, 675–687 (1991), the disclosures of which are hereby incorporated by reference. The foregoing methods can readily be adapted by one of ordinary skill in the art to provide a method of synthesizing the compounds of the present invention.

A preferred synthetic method includes the steps of preparing a compound of formula II

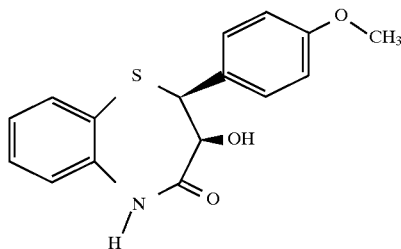

and reacting the compound with potassium carbonate in acetone and a compound selected from the group consisting of 2-chloroethanol, ethyl bromoacetate and 2-chloroethyl benzyl ether. The products generated from the reaction can further react with pyridine and acetic anhydride to give corresponding esters. Compounds of formula II can be obtained by methods known to those skilled in the art. Preferably, such compounds are obtained by reacting 2-aminothiophenol with a trans-3-arylglycidic ester.

Alternatively, the compounds of the present invention can be obtained by chemically modifying diltiazem. For example, LLU-β1 can be obtained by reacting diltiazem with methyl bromide followed by hydrolysis of the quaternary salt with base. Diltiazem is commercially available and is readily obtainable.

The following examples are intended to illustrate but not limit the invention. While they are typical of procedures that might be used, other procedures known to those skilled in the art may be alternatively employed.

EXAMPLE 1

Synthesis of Compounds of the Present Invention

1. The Synthesis of LLU-β1

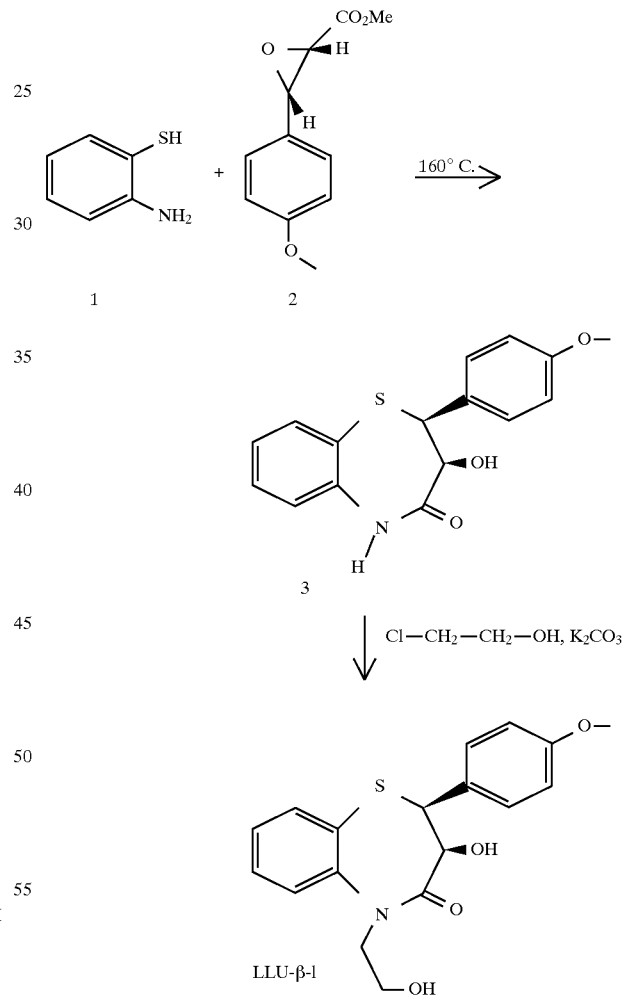

a. Synthesis of (2S,3S)-2,3-Dihydro-3-Hydroxy-2-(4-Methoxyphenyl)-1,5-Benzothiazepin-4(5H)-One A mixture of 2-aminothiophenol (1) (0.1 mol) and (S,S)-trans-3-arylglycidic ester (2) (0.11 mol) was heated at 160° C. for 16 hours. After cooling, the reaction mixture was tritiated with small amount of ethanol and recrystallized from ethyl acetate—hexane to give cis-lactam (3).

b. Synthesis of (2S,3S)-5-(2-Hydroxyethyl)-2,3-Dihydro-3-Hydroxy-2-(4-Methoxyphenyl)-1,5-Benzothiazepin-4(5H)-One (LLU-β1)

A mixture of 3 (0.5 mol), 2-chloroethanol (0.55 mol) and potassium carbonate (1.5 mol) was formed in acetone (500 mL) and heated at reflux for 2 hours. Acetone-insoluble compounds were filtered and the filtrate was concentrated. The residual oil was tritiated with diisopropyl ether and recrystallized from ethyl acetate—hexane to afford LLU-β1.

2.Synthesis of Benzyl and Acetyl Derivatives of LLU-β1
a. Synthesis of (2S,3S)-5-(2-Benzoxyethyl)-2,3-Dihydro-3-Hydroxy-2-(4-Methoxyphenyl)-1,5-Benzothiazepin-4(5H)-One A mixture of cis-lactam 3 (0.1 mol), 2-chloroethyl-benzyl ether (0.121 mol), potassium carbonate (0.3 mol), acetone (100 mL) and water (1 mL) was stirred vigorously under reflux for 17 hours. After cooling, inorganic compounds were filtered and the filtrate was concentrated. The residual oil was tritiated with diisopropyl ether and recrystallized from ethyl acetate—hexane to afford derivative 4.

b. Synthesis of (2S,3S)-5-(2-benzoxyethyl)-2,3-Dihydro-3-Acetyl-2-(4-Methoxyphenyl)-1,5-benzothiazepin-4(5H)-one Derivative 4 (0.01 mol) was dissolved in pyridine (20 mL) and acetic anhydride (10 mL) was added at 5° C. The reaction mixture was left at room temperature for 18 hours, and solvent was then removed in vacuum. The residue was dissolved in ethyl acetate (100 mL), washed with water (30 mL), citric acid (10%, 30 mL), water (30 mL), saturated NaHCO$_3$ solution (30 mL), and water (30 mL) and dried over sodium sulfate. Solvent was then removed and the residue crystallized from ethyl acetate—hexane, yielding derivative 5.

c. Synthesis of (2S,3S)-5-(2-Hydroxyethyl)-2,3-Dihydro-3-Acetyl-2-(4-Methoxyphenyl)-1,5-Benzothiazepin-4(5H)-One Derivative 5 (0.01 mol) was dissolved in a mixture of ethanol-water-acetic acid (9:1:0.1) and palladium on carbon catalyst (10% Pd, 1 g) was added. The compound was hydrogenated for 18 hours at room temperature and atmospheric pressure. The catalyst was filtered off, solvent was removed and the product was crystallized from ethyl acetate—hexane to afford derivative 6.

d. Synthesis of (2S,3S)-5-(2-Acetyl-Ethyl)-2,3-Dihydro-3-Acetyl-2-(4-Methoxyphenyl)-1,5-Benzothiazepin-4(5H)-One Derivative 6 or LLU-β1 (9.01 mol) was dissolved in pyridine (20 mL) and acetic anhydride (10 mL) was added at 5° C. The reaction mixture was left at room temperature for 18 hours, and solvent was the removed in vacuum. The residue was dissolved in ethyl acetate (100 mL), washed with water (30 mL), citric acid (10%, 30 mL), water (30 mL), saturated NaHCO$_3$ solution (30 mL), and water (30 mL) and dried over sodium sulfate. Solvent was removed and the residue was crystallized from ethyl acetate—hexane to afford derivative 7.

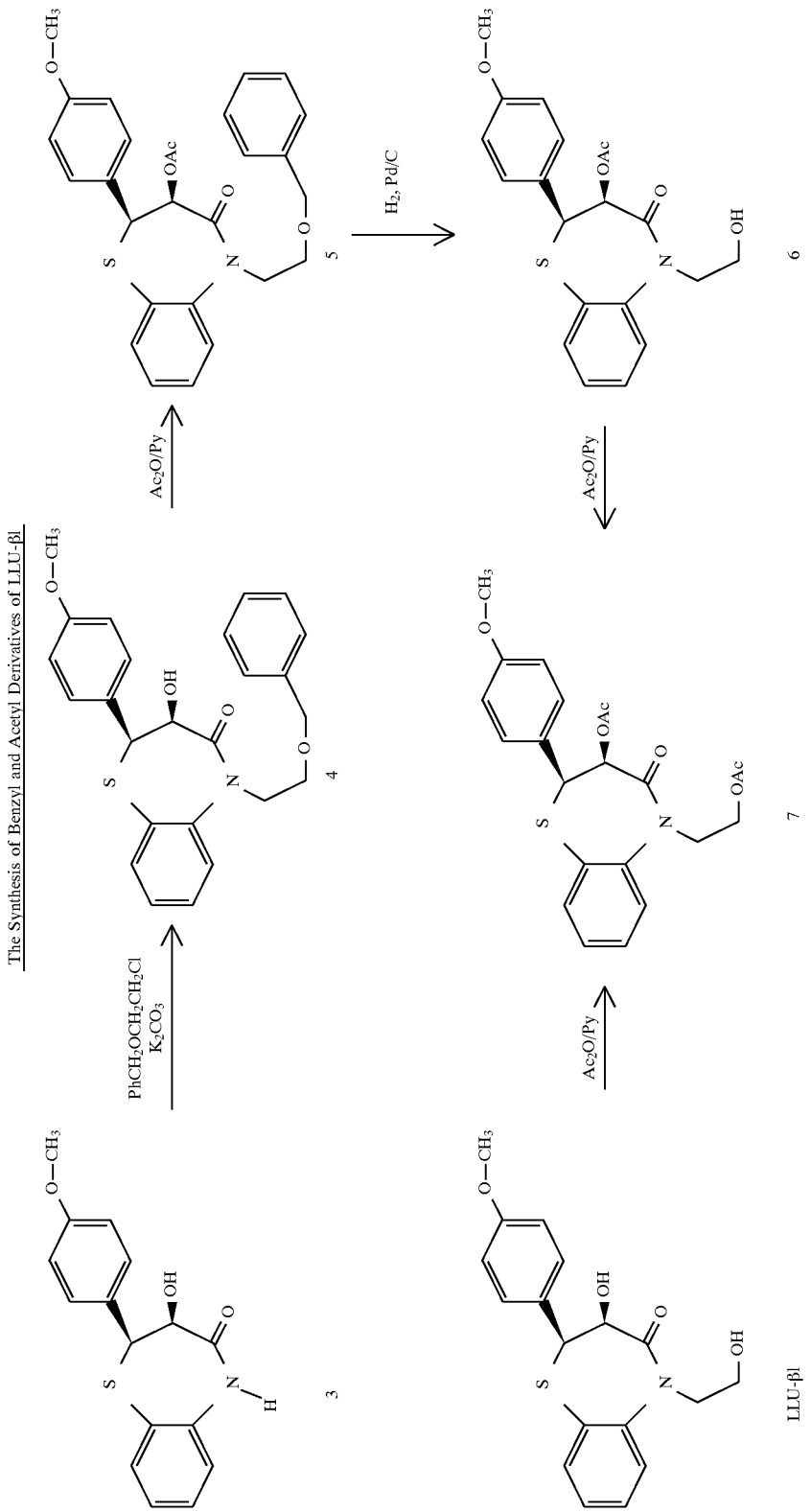

3. Alternative Path in Synthesis of LLU-β1 and Acetyl Derivatives a. Synthesis of (2S, 3S)-5-Ethylacetyl-2,3-Dihydro-3-Hydroxy-2-(4-Methoxyphenyl)-1,5-Benzothiazepin-4(5H)-One A mixture of cis-lactam 3 (0.1 mol), ethyl bromoacetate (0.11 mol), potassium carbonate (0.3 mol), and acetone (100 mL) was stirred vigorously under reflux for 1.5 hours. After cooling, inorganic compounds were filtered and the filtrate was concentrated. The residual oil was recrystallized from ethyl acetate and hexane to afford derivative 8.

b. Synthesis of (2S, 3S)-5-Acetic Acid-2,3-Dihydro-3-Hydroxy-2-(4-Methoxyphenyl)-1,5-Benzothiazepin-4(5H)-One A mixture of derivative 8 (0.1 mol), sodium hydroxide (0.2 mol), water (80 mL) and ethanol (300 mL) was stirred for 2 hours at room temperature. The reaction mixture was acidified with concentrated HCl and extracted with ethyl acetate. The extracts were combined, washed with water and dried over sodium sulfate, then solvent was removed. The residue was crystallized from aqueous ethanol, yielding derivative 9.

c. Synthesis of (2S, 3S)-5-Acetic Acid-2,3-Dihydro-3-Acetyl-2-(4-Methoxyphenyl)-1,5-Benzothiazepin-4(5H)-One Derivative 9 (0.01 mol) was dissolved in pyridine (20 mL) and acetic anhydride (10 mL) was added at 5° C. The reaction mixture was left at room temperature for 5 hours, and solvent was then removed in vacuum. The residue was dissolved in ethyl acetate (100 mL), washed with water (30 mL), citric acid (10%, 30 mL), water (30 mL), saturated $NaHCO_3$ solution (30 mL), and water (30 mL) and dried over sodium sulfate. Solvent was removed and the residue was crystallized from ethyl acetate—hexane to afford derivative 10.

d. Synthesis of (2S, 3S)-5-(2-Hydroxyethyl)-2,3-Dihydro-3-Hydroxy-2-(4-Methoxyphenyl)-1,5-Benzothiazepin-4(5H)-One (LLU-β1)

Derivative 9 (0.01 mol) was dissolved in dry tetrahydrofuran (20 mL), cooled in an ice-water bath and borane-tetrahydrofuran complex (0.012 mol) was added with stirring. The mixture was stirred for 2 hours at 5° C., then ice-water (0.02 mol) was slowly added. The solvent was removed in vacuum and the residue was dissolved in mixture of water and ethyl acetate (1:1, 200 mL). The water phase was once more extracted with ethyl acetate, and the combined extracts were washed with aqueous sodium bicarbonate solution, then with water, and dried over sodium sulfate. Solvent was then removed. The residue was crystallized from ethyl acetate to yield LLU-β1.

e. Synthesis of (2S,3S)-5-(2-Hydroxyethyl)-2,3-Dihydro-3-Acetyl-2(4-Methoxyphenyl)-1,5-Benzothiazepin-4(5H)-One Derivative 10 (0.01 mol) was dissolved in dry tetrahydrofuran (20 mL), cooled in an ice-water bath and borane-tetrahydrofuran complex (0.012 mol) was added with stirring. The mixture was stirred for 2 hours at 5° C., then ice-water (0.02 mol) was slowly added. The solvent was removed in vacuum and the residue was dissolved in a mixture of water and ethyl acetate (1:1, 200 mL). The water phase was once more extracted with ethyl acetate. The combined extracts were then washed with aqueous sodium bicarbonate solution, followed by water, and then dried over sodium sulfate. The solvent was removed, and the residue was crystallized from ethyl acetate to afford compound 11.

f. Synthesis of (2S, 3S)-5-(2-Acetylethyl)-2,3-Dihydro-3-Acetyl-2-(4-Methoxyphenyl)-1,5-Benzothiazepin-4(5H)-One LLU-β1 (0.01 mol) was dissolved in pyridine (20 mL) and acetic anhydride (10 mL) was added at 5° C. The reaction mixture was left at room temperature for 5 hours, and the solvent was removed in vacuum. The residue was dissolved in ethyl acetate (100 mL), washed with water (30 mL), citric acid (10%, 30 mL), water (30 mL), saturated $NaHCO_3$ solution (30 mL), and water (30 mL) and then dried over sodium sulfate. Solvent was removed and the residue was crystallized from ethyl acetate—hexane to yield compound 12.

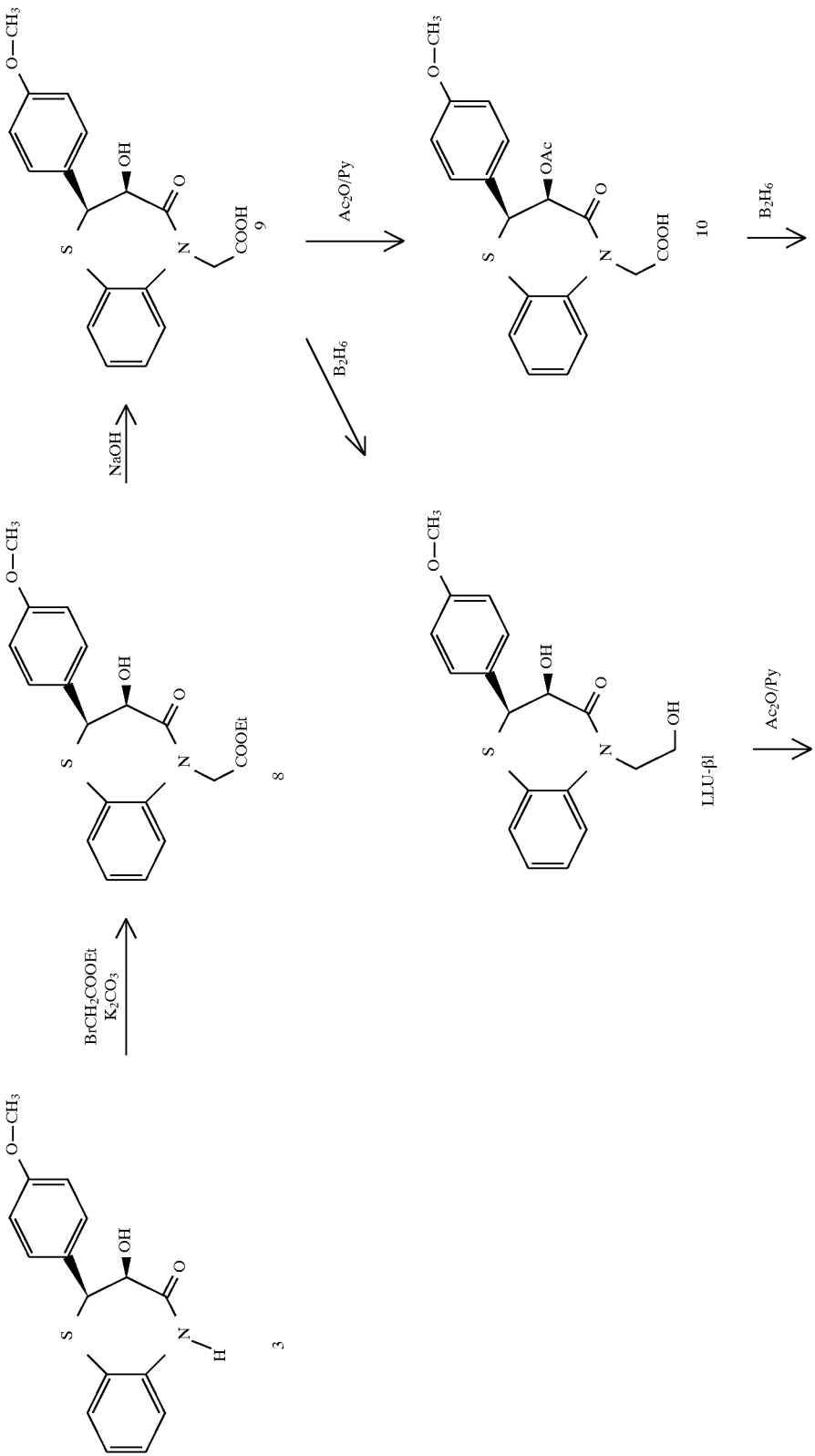

-continued
The Synthesis of LLU-βI and Acetyl Derivatives
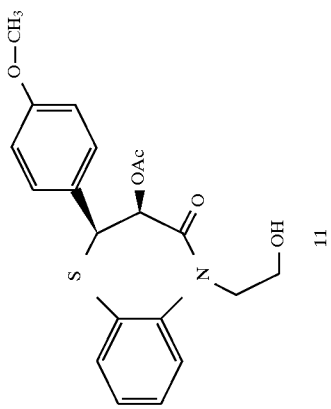
11
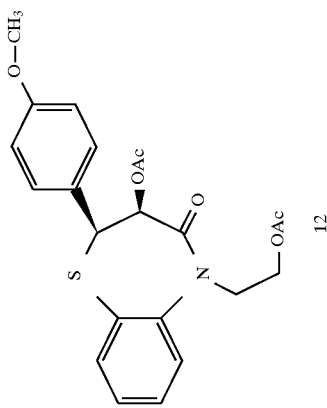
12

EXAMPLE 2

Bioassays for Biological Activity

1. In Vivo Bioassay

The assay for natriuresis in conscious rats has been described previously (see Benaksas et al., *Life Sciences*, v. 52, pp. 1045–1054 (1993)). The assay is briefly reiterated here. Female Sprague-Dawley (Harlan) rats (200–250 g) were cannulated in the femoral artery and vein for monitoring of mean arterial pressure (MAP) and infusion of saline and samples, respectively. The bladder was catheterized for collection of urine in ten-minute periods. Furosemide (0.4 mg/kg bwt; 1 mg/mL in 0.17% saline) was infused as a positive control at the beginning of the sixth ten-minute period. The sample was infused at the beginning of the seventeenth ten-minute period. Urine was collected for another 150 minutes. The volume of the urine was determined gravimetrically and the $Na^+$ and $K^+$ concentrations determined with a Beckman E2A electrolyte analyzer. From these data the sodium excretion values (UNaV) were calculated.

The natriuretic response of a sample was normalized to the dose of furosemide infused. The net sodium excretion for the infusion of furosemide or sample was calculated as follows. The median sodium excretion value ($\mu$moles $Na^+$/10 minute period—baseline $\mu$moles $Na^+$ for the five periods before infusion of furosemide or sample was used to establish a baseline value for the calculation of $\Delta UNaV$ (=$\mu$moles $Na^+$ period) for administration of either furosemide or sample respectively. The sum of $\Delta UNaV$ for the four periods following infusion of furosemide was the net sodium excreted for furosemide, defined as FR. The sum of $\Delta UNaV$ for the fifteen periods following infusion of the sample was the net sodium excreted for the sample defined as SR. The natriuretic ratio $R_n$ (or normalized natriuretic response) of a sample was calculated by dividing SR by FR ($R_n$=SR/FR). A sample is considered natriuretically active if the $R_n$ value for that sample was greater than or equal to 0.67 (greater than 99% confidence limits).

Although the invention has been described with reference to the presently preferred embodiment, it should be understood that various modifications can be made without departing from the spirit of the invention. Accordingly, the invention is limited only by the following claims.

What is claimed is:

1. A compound having the formula

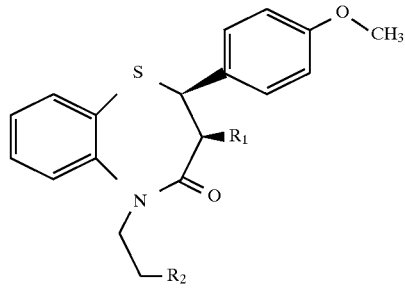

in which $R_1$, $R_2$ independently are OH, OOC—$R_3$ or O—$R_3$, and $R_3$ is a $C_1$–$C_6$ alkyl, alkenyl, alkynyl or phenyl group which is unsubstituted or substituted with an alkyl, aryl, alkaryl, aralkyl, or halogen group, with the provisos that $R_1$ and $R_2$ are not both OOC—$CH_3$, and that when $R_1$ is OOC—$CH_3$, $R_2$ is not OH.

2. The compound of claim 1, wherein said $R_1$ and $R_2$ are OH.

3. A method of treating a mammal suffering from hypertension, congestive heart failure, renal disease, said method comprising the step of orally or parenterally administering to said mammal a pharmaceutical composition comprising a pharmaceutically acceptable carrier and a therapeutically effective amount of a compound having the formula

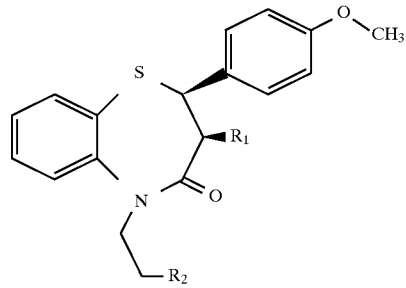

in which $R_1$, $R_2$ independently are OH, OOC—$R_3$ or O—$R_3$, and $R_3$ is a $C_1$–$C_6$ alkyl, alkenyl, alkynyl or phenyl group which is unsubstituted or substituted with an alkyl, aryl, alkaryl, aralkyl, or halogen group with the provisos that $R_1$ and $R_2$ are not both OOC—$CH_3$, and that when $R_1$ is OOC—$CH_3$, $R_2$ is not OH.

4. A pharmaceutical composition comprising a pharmaceutically acceptable carrier and a therapeutically effective amount to stimulate sodium excretion of a compound of claim 1.

5. A method of stimulating sodium excretion in the urine of a mammal suffering from an edematous condition, said method comprising the step of orally or parenterally administering to said mammal a pharmaceutical composition comprising a pharmaceutically acceptable carrier and a therapeutically effective amount of a compound having the formula

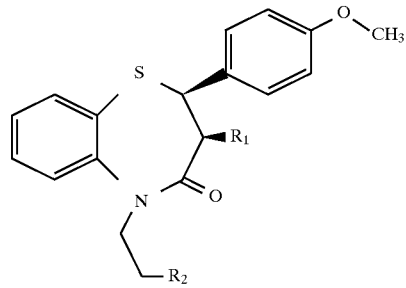

in which $R_1$, $R_2$ independently are OH, OOC—$R_3$ or O—$R_3$, and $R_3$ is a $C_1$–$C_6$ alkyl, alkenyl, alkynyl or phenyl group which is unsubstituted or substituted with an alkyl, aryl, alkaryl, aralkyl, or halogen group with the provisos that $R_1$ and $R_2$ are not both OOC—$CH_3$, and that when $R_1$ is OOC—$CH_3$, $R_2$ is not OH.

* * * * *